United States Patent
Bienstman et al.

(10) Patent No.: US 9,671,335 B2
(45) Date of Patent: Jun. 6, 2017

(54) PHOTONICS INTEGRATED INTERFEROMETRIC SYSTEM AND METHOD

(71) Applicants: UNIVERSITEIT GENT, Ghent (BE); IMEC, Leuven (BE)

(72) Inventors: Peter Bienstman, Ghent (BE); Tom Claes, Ghent (BE)

(73) Assignees: UNIVERSITEIT GENT, Ghent (BE); IMEC VZW, Leuven (BE)

( * ) Notice: Subject to any disclaimer, the term of this patent is extended or adjusted under 35 U.S.C. 154(b) by 399 days.

(21) Appl. No.: 14/135,713

(22) Filed: Dec. 20, 2013

(65) Prior Publication Data

US 2014/0176957 A1 Jun. 26, 2014

(30) Foreign Application Priority Data

Dec. 20, 2012 (EP) ..................................... 12198787

(51) Int. Cl.
   *G01N 21/45* (2006.01)
(52) U.S. Cl.
   CPC ....... *G01N 21/45* (2013.01); *G01N 2021/458* (2013.01)
(58) Field of Classification Search
   CPC ........................... G01N 2021/458; G01N 21/45
   See application file for complete search history.

(56) References Cited

U.S. PATENT DOCUMENTS

| | | | | |
|---|---|---|---|---|
| 7,602,500 B2* | 10/2009 | Izatt | ...... | A61B 3/102 356/497 |
| 2005/0135723 A1* | 6/2005 | Carr | ...... | G01N 21/45 385/12 |
| 2007/0002327 A1* | 1/2007 | Zhou | ...... | A61B 3/102 356/456 |
| 2012/0214707 A1 | 8/2012 | Ymeti et al. | | |
| 2013/0094029 A1* | 4/2013 | Bienstman | ...... | G01N 21/41 356/517 |

OTHER PUBLICATIONS

Search Report from Corresponding EP Application No. 13197306.7, Apr. 10, 2014.
Search Report from corresponding EP Application No. 12198787, May 8, 2013.
(Continued)

*Primary Examiner* — Hwa Lee
(74) *Attorney, Agent, or Firm* — Workman Nydegger (57) ABSTRACT

A photonics integrated system is disclosed, comprising a substrate, an integrated interferometer integrated in the substrate and being configured for receiving radiation from a radiation source, and an integrated spectral filter integrated in the substrate and being configured for receiving radiation from the interferometer. The integrated interferometer has a period and the integrated spectral filter has a bandwidth such that the period of the integrated interferometer is smaller than the bandwidth of the integrated spectral filter. The integrated spectral filter has a periodic transfer characteristic with a period and the system has a bandwidth such that the period of the periodic transfer characteristic of the integrated spectral filter is larger than the bandwidth of the system.

13 Claims, 4 Drawing Sheets

(56) References Cited

OTHER PUBLICATIONS

Luff, B.J., et al., "Integrated Optical Mach-Zehnder Biosensor", Journal of Lightwave Technology, vol. 16, No. 4, Apr. 1998, pp. 583-592.
Bernini, Romeo, et al., "Generalized Mach-Zehnder Interferometers for Sensing Applications", Sensors and Actuators B: Chemical, International Journal Devoted to Research and Development of Physical and Chemical Transducers, Elsevier S.A., Switzerland, vol. 100, No. 1-2, Feb. 18, 2004, pp. 72-74.
Claes, Tom, et al., "Vernier-Cascade Label-Free Biosensor with Integrated Arrayed Waveguide Grating for Wavelength Interrogation with Low-Cost Broadband Source", Optics Letters, vol. 36, No. 17, Sep. 1, 2011, pp. 3320-3322.
Castello, J.G., et al., "Real-Time and Low-Cost Sensing Technique Based on Photonic Bandgap Structures", Optics Letters, vol. 36, No. 14, Jul. 15, 2011, pp. 2707-2709.
Xia, Zhixuan, et al., "Silicon Microring Resonator Sensor with Integrated PC Spectrometer for Sharp Spectral Features Detection", 23rd Annual Meeting of the IEEE Photonics Society, Nov. 7-11, 2010, pp. 329-330.

\* cited by examiner

PHOTONICS INTEGRATED INTERFEROMETRIC SYSTEM AND METHOD

FIELD OF THE INVENTION

The invention relates to the field of photonic integrated sensors. More specifically it relates to methods and systems for detection and/or quantification of chemical, biological or biochemical targets, such as for example evanescent wave sensors.

BACKGROUND OF THE INVENTION

Cheap label-free integrated photonics sensors have been demonstrated that allow fast and accurate quantitative detection of biologically relevant molecules (biosensors) for applications in medical diagnostics and drug development or volatile compounds (gas sensors) for applications in environmental sensing, medical diagnostics or air quality sensing or other environmental changes such as temperature, stress, pressure, pH, etc.

Different integrated optical sensors are used. Ring resonator sensors, microdisk sensors and grating-coupled waveguide sensors have been widely used. Interferometric sensors are very attractive for biosensing due to their high sensitivity and broad dynamic range. Mach-Zehnder (MZI), Young (YI) and Hartman interferometers are the usual configurations employed for sensing.

However, whereas the sensor chip can be made cheaply, an expensive tunable laser or an optical spectrum analyser (OSA) is typically required to accurately monitor spectral shifts in the sensor's transmission spectrum (wavelength interrogation). Tuneable lasers and optical spectrum analysers are not only very expensive, they are bulky and heavy, making them not suitable for the development of compact and portable lab-on-a-chip (LOC) devices. In addition, these readout configurations may take several seconds to even minutes to acquire each sensor's spectrum, limiting the practical use of highly multiplexed configurations. Some approaches have been reported that enable the use of a cheap broadband light source, however all of them showing some limitations.

Figure 1A:
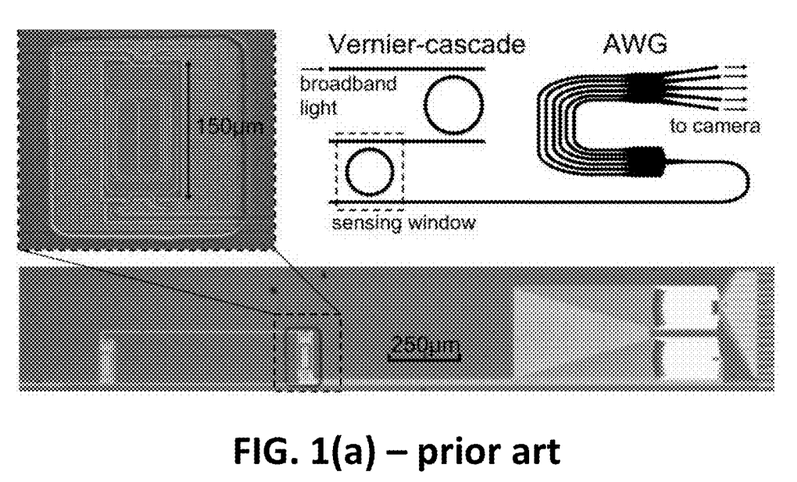
FIG. 1(a) and FIG. 1(b)—prior art—illustrate a schematic overview and exemplary integrated photonic sensor making use of a Vernier cascade sensor, as well as the obtained transmission spectrum used, as known from prior art.
Figure 1B:
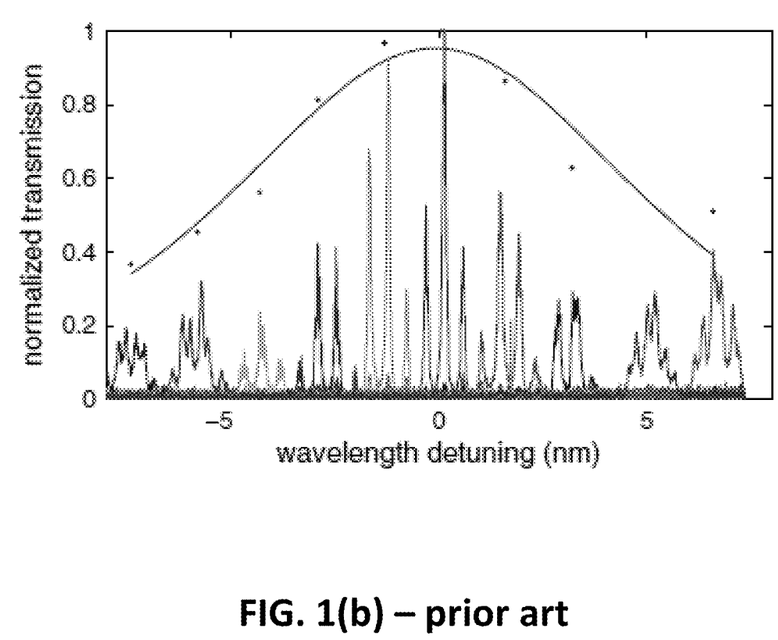

In Optics Letters 36 p 3320-3322 (2011), Claes et al. (see FIG. 1(a) and FIG. 1(b)) reported a very sensitive Vernier-cascade sensor with an arrayed waveguide grating (AWG) spectral filter that divides the sensor's transmission spectrum in multiple wavelength channels and transmits them to spatially separated output ports, allowing wavelength interrogation with a much cheaper broadband light source. Experiments show that this sensor can monitor refractive index changes of watery solutions in real time with a detection limit ($1.6 \cdot 10^{-5}$ RIU) competitive with more expensive interrogation schemes, indicating its applicability in low-cost label-free biosensing. However, using a Vernier-cascade sensor, most of the optical power that is coupled into the optical chip from the broadband light source is not used, because of the peaked nature of the spectrum. The transmission spectrum of a Vernier-cascade consists of sharp constituent peaks that are modulated with a periodic envelope signal. The shift of the envelope function is related to the change of the effective refractive index of the waveguide mode in the sensor ring. It is this shift that is measured and analyzed to detect quantitatively biologically relevant molecules or volatile compounds. The power that is available for this analysis is limited due to the comb-like Vernier transmission spectrum. Although this approach might work for a limited number of sensors, multiplexing of several sensors that are all analysed with a single broadband source is not possible due to the limited optical power budget. The power that reaches the detector approaches or is lower than the dark current noise of the detectors.

Another integrated scheme that was disclosed is a ring resonator sensor integrated with a photonic crystal spectral filter reported in IEEE Photonics annual meeting (2010) pp 329-330 by Xia et al. Since the sensitivity of a ring resonator in comparison with a Vernier configuration is a couple of orders of magnitude lower, the performance of ring resonators that are read out with an integrated spectral filter is unacceptable for practical applications.

Figure 2:
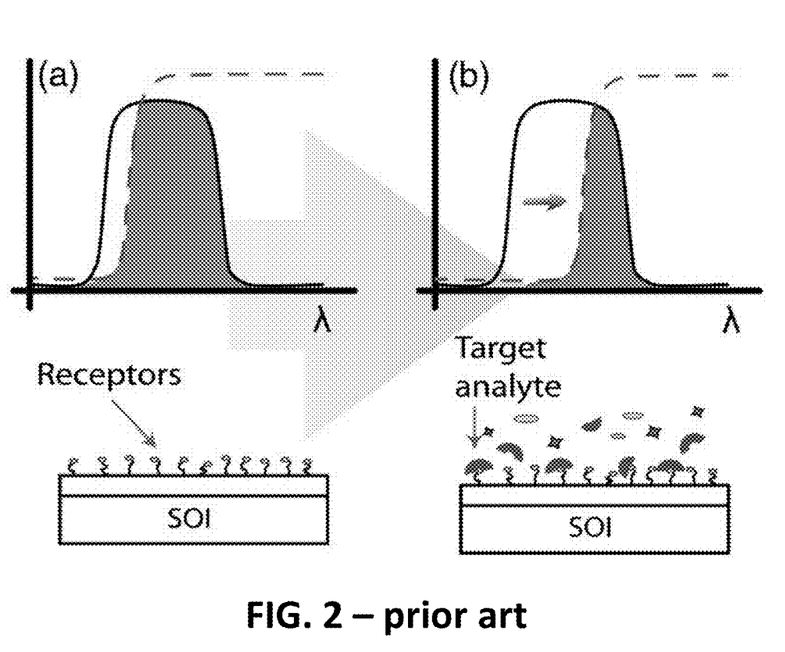
FIG. 2 illustrates the detection principle of a power-based read-out technique as known from prior art.

The use of power-based read-out techniques has been presented in the past as an alternative solution to wavelength interrogation method. An example thereof has been described in Optics Letters 36 (2011) pp 2707-2709 by Castello et al. The working principle of this technique is schematically illustrated in FIG. 2. Instead of directly measuring the position of the spectral resonance or envelope (i.e. based on the sensor transmission curve) and tracking its shift, this wavelength shift is indirectly tracked by measuring the variation of the output power. This is achieved by exciting the sensor using a filtered broadband source (with a certain bandwidth), which is aligned with the edge of the sensor transmission curve. The overlap between the source and the sensing structure determines the amount of output power. A change of the refractive index on the sensor's surface, which might be due to the binding of a target analyte or adsorption of a target compound or other environmental change, provokes a shift of the position of the sensor transmission curve, leading to a variation of the output power, which is directly used to perform the sensing. Indeed, this approach avoids the use of a tunable laser or an optical spectrum analyser (OSA) for the readout. However, the limit of detection (LOD) is deteriorated due to the non-linear response or non-linear relation between the detected optical power and the wavelength shift. Additionally, such a configuration becomes susceptible to power fluctuations in the source. Moreover, the need to align the sensor's transmission spectrum to the spectrum of the source or detector makes this configuration impractical.

There is still a need for an efficient and easy to use integrated photonics sensor that can be read out in a cheap way.

SUMMARY OF THE INVENTION

It is an object of embodiments of the present invention to provide good integrated photonics sensors and methods of using them.

It is an advantage of embodiments of the present invention that an integrated photonics sensor can be provided that can make use of a broad band radiation source. It is an advantage that there is no need for an expensive and complex tunable laser and/or an expensive external optical spectrum analyser.

It is an advantage of embodiments of the present invention that an integrated photonics sensor can be provided that is not significantly limited by the power budget, so that accurate and efficient detection can be obtained.

It is an advantage of embodiments of the present invention that an integrated photonics sensor can be provided that does not need tuning of the source, filter and detector spectra during use.

It is an advantage of embodiments of the present invention that a system with a lab-on-chip spectrum analyser can be provided with good performance, e.g. a performance comparable to a system with a stand-alone spectrum analyser.

It is an advantage of embodiments of the present invention that a system with a lab-on-chip spectrum analyser can be provided with a good detection limit, e.g. a detection limit comparable to that of ring resonators, while avoiding the need for having a costly and complex tunable radiation source, such as for example a tunable laser.

The above objective is accomplished by a method and device according to the present invention.

The present invention relates to a photonics integrated system, the photonics integrated system comprising a substrate, an integrated interferometer integrated in the substrate and being configured for receiving radiation from a radiation source, and an integrated spectral filter integrated in the substrate and being configured for receiving radiation from the interferometer, wherein the integrated interferometer has a period and the integrated spectral filter has a bandwidth such that the period of the integrated interferometer is smaller than the bandwidth of the integrated spectral filter, and wherein the integrated spectral filter has a periodic transfer characteristic and the system has a bandwidth The period of the periodic transfer characteristic of the integrated spectral filter is larger than the bandwidth of the system. The bandwidth typically may be selected to correspond to the useful range of wavelengths that can be considered in the system. The bandwidth thus typically may fit within the period of the integrated spectral filter thus making optimal use of the available bandwidth and avoiding aliasing. It is an advantage of embodiments according to the present invention that due to codesign of the interferometer and the spectral filter, a high performance (low detection limit) integrated system can be obtained wherein good use can be made of the available power budget.

The integrated interferometer may be a Mach-Zehnder interferometer. It is an advantage of embodiments of the present invention that use can be made of a known optical component for obtaining the special design according to embodiments of the present invention.

The integrated spectral filter may be an arrayed waveguide grating. It is an advantage of embodiments of the present invention that use can be made of a known optical component for obtaining the special design according to embodiments of the present invention.

The photonics integrated system may comprise an integrated spectral analyser comprising the integrated spectral filter.

The system furthermore may comprise a read-out means for reading out a multiple of channels of the spectrum analyser in parallel. It is an advantage of embodiments of the present invention that parallel read-out can be obtained, allowing to measure substantially quicker than in known integrated systems. The latter allows averaging over a large number of measurements leading to a better noise behavior than when use is made of a tunable laser or when using an external spectrum analyser where typically sequential measurement is used.

The read-out means may be a multiple pixel camera for imaging output couplers in each of the channels of the spectrum analyser in parallel. It is an advantage of embodiments of the present invention that a multi-pixel camera can be used which are well known optical components. Furthermore, such components advantageously also can be introduced in the substrate. The system furthermore may comprise an integrated radiation source integrated in the substrate configured for providing radiation to the integrated interferometer. It is an advantage of embodiments of the present invention that full integration of both source, sensor and analyser can be obtained. The latter assists in having a compact device, that has high portability.

The integrated radiation source may be a broad band radiation source. Alternatively, another, non-integrated broad band radiation source also may be used. It is an advantage of embodiments of the present invention that the complexity on source requirements compared to other systems is relaxed, offering the possibility of having a low cost device.

The system may be a sensor wherein the integrated interferometer may comprise at least a first radiation waveguide and a second radiation waveguide split off from a common radiation path upstream and recombined in a single path downstream, and whereby the first radiation waveguide is configured as a sensing region for interaction with an analyte to be studied and the second radiation waveguide is configured to be screened off from the analyte to be studied. It is an advantage of embodiments of the present invention that use can be made of a simple but smart design for obtaining the advantageous properties being high sensitivity, good accuracy, low limit-of-detection and good use of power budget.

The sensing region may comprise receptors for target analytes of interest. It is an advantage of embodiments of the present invention that use can be made of well known techniques for bringing target analytes of interest in the environment of or in the sensing region.

The first and/or the second radiation waveguide may be folded or curved waveguides. It is an advantage of embodiments of the present invention that use can be made of known photonics integrated circuits techniques for implementing the smart design as described in embodiments of the present invention.

The present invention also relates to a system for detecting a biological, chemical, biomimic or biochemical target analyte in a medium, the system comprising a photonics integrated system as described above.

The present invention also relates to the use of a photonics integrated system as described above for detection of analytes in a specimen.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

The drawings are only schematic and are non-limiting. In the drawings, the size of some of the elements may be exaggerated and not drawn on scale for illustrative purposes.

Any reference signs in the claims shall not be construed as limiting the scope.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn on scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to radiation, reference is made to electromagnetic radiation. The radiation envisaged is in principle not limited and may be any useful wavelength or wavelength range for detection or sensing applications envisaged. Some examples of radiation ranges that are envisaged, embodiments of the present invention not being limited thereto, are visual radiation, infrared radiation, near infrared radiation and mid infrared radiation.

Where in embodiments of the present invention reference is made to a photonics integrated circuit or system, reference is made to a variety of forms and material systems such as for example low-index contrast waveguide platforms, e.g. polymer waveguides, glass/silica waveguides, $Al_xGa_{1-x}As$ waveguides, $In_xGa_{1-x}As_yP_{1-y}$ waveguides or SiN waveguides, high-index contrast waveguide platforms, e.g. Silicon-on-Insulator or semiconductor membranes, or plasmonic waveguides, or waveguides based on silicon, germanium, silicon germanium, silicon nitride, silicon carbide, etc. Silicon-on-Insulator, is a very interesting material system for highly integrated photonic circuits. The high refractive index contrast allows photonic waveguides and waveguide components with submicron dimensions to guide, bend and control light on a very small scale so that various functions can be integrated on a chip. Such waveguides allow a high level of miniaturization, which is advantageous. Furthermore for such waveguide types radiation can be efficiently coupled in and out the photonics integrated circuit. Using Silicon-on-insulator also has some technological advantages. Due to the CMOS industry, silicon technology has reached a level of maturity that outperforms any other planar chip manufacturing technique by several orders of magnitude in terms of performance, reproducibility, throughput and cost. Nano-photonic ICs can be fabricated with wafer scale-processes, which means that a wafer can contain a large number of photonic integrated circuits.

When in embodiments of the present invention reference is made to a photonics integrated interferometric sensor or photonics integrated interferometric circuit, reference is made to an optical circuit comprising at least one integrated interferometer, i.e. having an interferometer integrated in the substrate. Further components also may be integrated such as an integrated optical cavity, a further integrated optical resonator, an integrated optical interferometer, an integrated optical coupler, a waveguide, a taper, a tunable filter, a phase-shifter, a grating, a modulator, a detector, a light source or a combination thereof.

Figure 4:
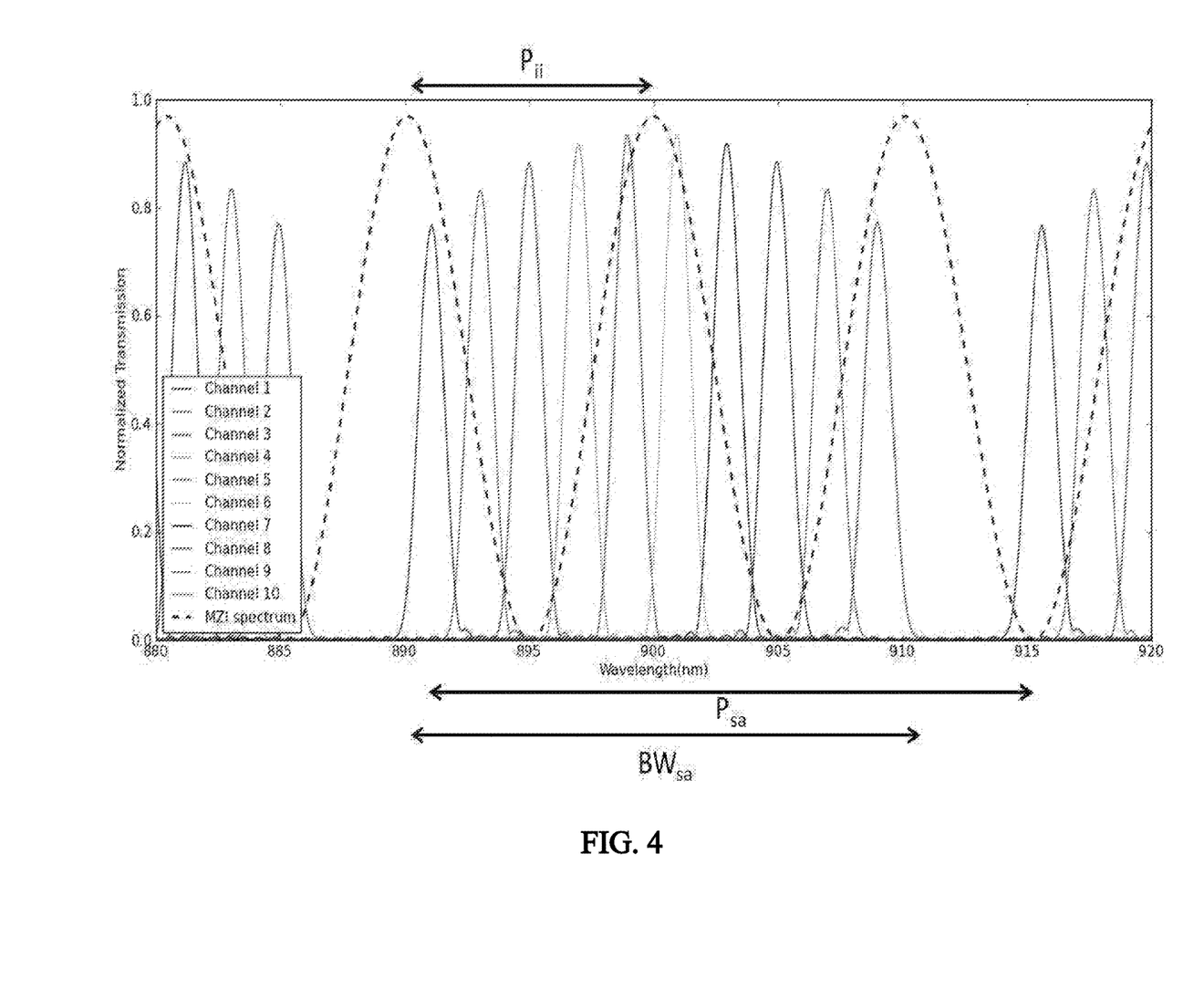
FIG. 4 shows a schematic overview of the parameters of the system as used for co-designing the integrated interferometer and the integrated spectral filter according to an embodiment of the present invention.

When in embodiments of the present invention reference is made to a photonics integrated spectral filter or photonics integrated spectral analyser, reference is made to an optical circuit comprising the optical components to demultiplex an optical signal into at least 2 spectral bands, each coupled to a different channel. The aggregated bandwidth of the spectral bands is the bandwidth of the spectral analyser. In other words, the bandwidth of the spectral analyser typically may be determined by the aggregation of the bandwidth of the different spectral bands used in the system. The bandwidth of the entire system (i.e. source+integrated circuit+detector) can be furthermore limited by the bandwidth of the source, the bandwidth of the incoupling and outcoupling structure.

Where in embodiments of the present invention reference is made to the detection limit of a refractive index sensor, reference is made to the smallest change of the refractive index that can be detected. The sensitivity of the sensor is indicative of the amount of change in the detection signal in the sensor for a given amount of targets to be sensed.

Where in embodiments of the present invention reference is made to a period of an interferometric component, also referred to as interferometer, reference is made to the period (as a function of wavelength) of the transmission spectrum of the interferometric component. The period also is indicated in FIG. 4.

Where in embodiments of the present invention reference is made to the period of the spectral filter or spectral analyser comprising the filter, reference is made to the period (as a function of wavelength) of the transmission spectrum of the filter component, i.e. to the period of a periodic transfer function of the filter component allowing for the fact that some spectral regions of the function are not served by filter channels. The period also is indicated in FIG. 4.

Where in embodiments of the present invention reference is made to the bandwidth of the spectral filter or spectral analyser comprising the filter, reference is made to the total spectral bandwidth of the combination of all the channels in the filter. The bandwidth also is indicated in FIG. 4.

Where in embodiments of the present invention reference is made to the bandwidth of the system, reference is made to the total spectral bandwidth of the complete system, which can be limited by factors like bandwidth of the source, bandwidth of in- and outcoupling gratings, . . . .

In a first aspect, the present invention relates to a photonics integrated interferometric system. Such a photonics integrated system, allows radiation processing on chip and advantageously also spectral radiation processing. The photonics integrated system may in some embodiments be a lab-on-chip system, allowing besides radiation processing on the chip also sample processing on chip. Lab-on-chip systems, have the advantage of being compact and consequently very portable. According to embodiments of the present invention, the photonics integrated interferometric system comprises a substrate, the substrate comprising, integrated therein, an interferometer configured for receiving radiation from a radiation source, e.g. broadband radiation source, and a spectral filter integrated in the substrate and configured for receiving radiation from the interferometer. According to embodiments of the present invention, in the system, the integrated interferometer (130) has a period ($P_{ii}$) and the integrated spectral filter (140) has a bandwidth ($BW_{sa}$) such that the period ($P_{ii}$) of the integrated interferometer (130) is smaller than the bandwidth ($BW_{sa}$) of the integrated spectral filter (140). Furthermore, the integrated spectral filter (140) has a periodic transfer characteristic having a period ($P_{sa}$) and the system has a bandwidth ($BW_{system}$) such that the period ($P_{sa}$) of the periodic transfer characteristic of the integrated spectral filter (140) is larger than the bandwidth ($BW_{system}$) of the system (100)

This special co-design results in advantageously accurate and sensitive integrated spectral systems.

Figure 3:
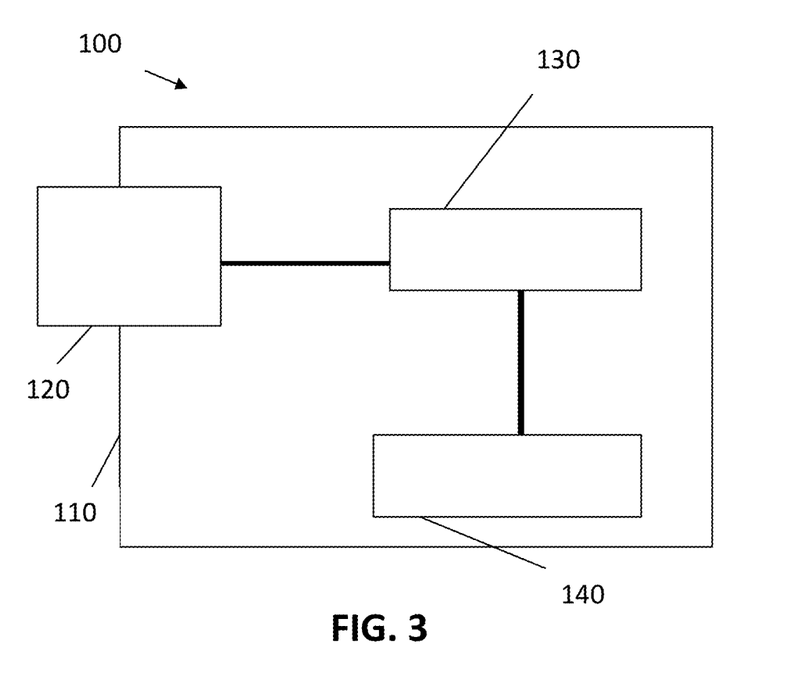
FIG. 3 shows a schematic overview of an exemplary photonic integrated interferometric system according to an embodiment of the present invention.

By way of illustration, embodiments of the present invention not being limited thereto, different components will now be further described with reference to FIG. 3, showing a schematic representation of a system 100 according to an embodiment of the present invention, indicating standard and optional components.

The photonics integrated interferometric system 100 comprises a substrate 110. Such a substrate may be any suitable substrate, as known by the person skilled in the art, e.g. as described above. The substrate may in some regions be adapted for acting as a sensing surface. More particularly, typically at least part of the interferometer described further, will be positioned in a sensing region. Techniques for rendering a region sensitive for particular analytes of interest are known to the person skilled in the art. The surface may for example be provided with receptors. The surface of the sensor device thus may be modified by elements or with a coating which is designed to attract certain molecules or may be modified by attaching molecules to it, which are suitable to bind the target molecules which are present in the sample fluid. Such molecules are known to the skilled person. The surface of the sensor device can also be provided with molecules in the form of organisms (e.g. viruses or cells) or fractions of organisms (e.g. tissue fractions, cell fractions, membranes). The surface of biological binding can be in direct contact with the sensor chip, but there can also be a gap between the binding surface and the sensor chip. For example, the binding surface can be a material that is separated from the chip, e.g. a porous material, or the binding elements may be positioned at a surface near the substrate but not on the substrate.

Figure 5:
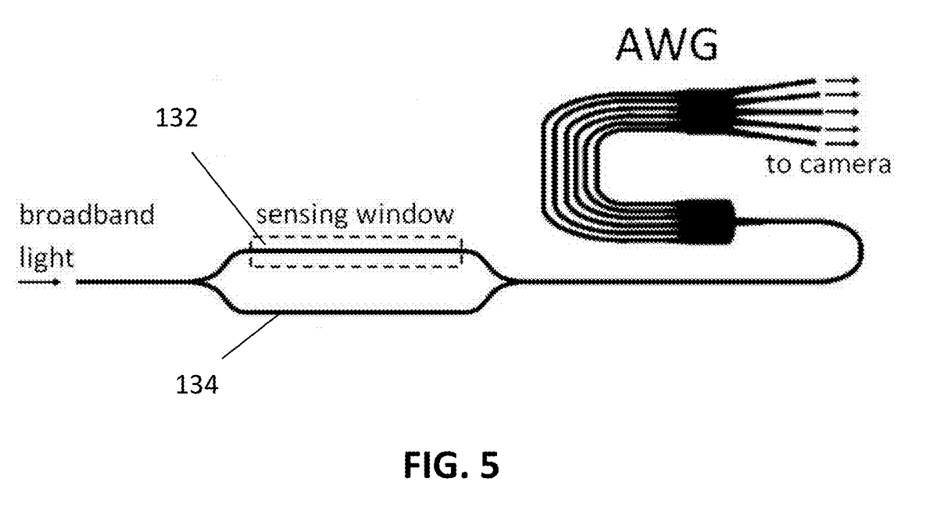
FIG. 5 shows a schematic overview of an exemplary system based on a Mach-Zehnder interferometer and an arrayed waveguide grating, according to an embodiment of the present invention.

The interferometric sensor 100 according to embodiments of the present invention comprises an integrated interferometer 130. Such an integrated interferometer 130 is integrated in the substrate 110, e.g. in a homogeneous or heterogeneous manner. Advantageously, similar techniques may be used as for processing the other parts of the substrate, e.g. using CMOS techniques. The interferometer 130 may be any suitable interferometer 130 for example be based on an integrated Mach-Zehnder interferometer (MZI), Young interferometer (YI) or Hartman interferometer. In one set of embodiments, an integrated Mach-Zehnder interferometer thus is used. The integrated Mach-Zehnder interferometer comprises an input optical waveguide (common waveguide) that is split into two waveguide arms 132, 134 which are recombined again after a certain distance in an output optical waveguide. The latter is illustrated in FIG. 5 by way of example. Typically one waveguide arm 134 is taken as a reference—referred to as the reference arm—and one waveguide arm 132 is used for sensing—referred to as the sensing arm. A sensing region may then typically be positioned within the evanescent field region of the optical waveguide arm 132. In practice the presence of analytes is determined based on an interference signal. More particularly, assuming that the optical path length for both waveguide arms is equal, radiation that will travel through both arms will recombine thereafter without phase difference. If nevertheless, e.g. due to presence of analytes, the environment in one of the arms changes and this induces a change in refractive index, the difference in refractive index will lead to a phase difference between the two radiation subwaves travelling through the different waveguide arms. Consequently, recombining these subwaves will result in an interference signal, whereby the intensity of this signal is given by $$I(\lambda) = \cos^2\left(\frac{\Delta n_{eff} \pi L}{\lambda}\right)$$

with $\Delta n_{eff}$ the difference in refractive index, L being the length of the waveguide arms, I being the intensity and $\square$ being the wavelength of the radiation. In some embodiments, an optimized interferometer may be used, whereby temperature noise can also be reduced. The latter can be obtained by providing a length difference between the different waveguide arms of the interferometer that is selected so that the following equation is fulfilled $$\frac{\delta n_{eff\_ref}}{\delta T}(L - \Delta L) = \frac{\delta n_{eff\_sens}}{\delta T}$$

with $n_{eff\_ref}$ and $n_{eff\_sens}$ being the effective index of the reference respectively the sensing waveguide and $\Delta L$ being the difference in length for the sensing waveguide (additional length not being positioned in the sensing region)

A chemical, biochemical, biomolecular or molecular interaction in the sensing region will thus produce a variation in the effective refractive index for the radiation propagating through this area, inducing a phase difference between the radiation travelling in the sensing waveguide arm and the radiation travelling in the reference arm.

According to embodiments of the present invention, the integrated interferometer 130 is coupled to an on chip spectral filter 140, e.g. being part of a spectral analyser 142 or forming the spectral analyser 142. This spectral filter 140 can be any suitable on chip spectral filter 140, such as for example an arrayed waveguide grating (AWG), a planar concave grating demultiplexer (PCG), an echelle grating, . . . . The spectral filter 140 is integrated on the substrate. The latter may be a heterogeneous integration or a homogeneous integration. According to some embodiments of the present invention, such integration may be performed using CMOS compatible techniques also used for processing other parts of the substrate.

It was surprisingly found that by co-designing the interferometer and the spectrum analyser, an advantageous setup could be reached allowing fully resolving the spectrum and avoiding loss of salient features of the transmission spectrum of the radiation passing the interferometer. The co-design was performed such that the integrated interferometer 130, e.g. Mach-Zehnder interferometer, has a period $P_{ii}$ that is smaller than the bandwidth $BW_{sa}$ of the spectrum analyser. This condition can be expressed as follows, with $P_{ii}$ being the period of the integrated interferometer and $BW_{sa}$ the bandwidth of the integrated spectrum analyser, $$P_{ii} < BW_{sa}$$

The condition overcomes the problems typically associated with integrated spectral filters.

The parameters used in the condition are also illustrated in FIG. 4, illustrating the period of the integrated interferometer $P_{ii}$ and the bandwidth of the integrated spectrum analyser $BW_{sa}$. In the particular example shown $P_{ii}$ is 10 nm, $BW_{SA}$ is 20 nm and $P_{SA}$ is 24.5 nm. It will be clear that these values are only given by way of example, and that embodiments of the present invention are not limited thereby.

The system also is co-designed such that it advantageously fulfills the condition that the period of the spectrum analyser is larger than the bandwidth of the full system, this bandwidth being determined by the combination of the radiation source, the optical components such as e.g. possible grating couplers used, etc. This condition allows to make better use of the power budget than is e.g. possible using a Vernier configuration. This condition is expressed as $$P_{sa} > BW_{system}$$

with $P_{sa}$ being the period of the spectrum analyser, also referred to as the period of the periodic transfer characteristic of the integrated spectral filter, and $BW_{system}$ being the bandwidth of the system.

It is an advantage of embodiments of the present invention that the overall detection limit of the lab-on-chip system can be comparable to that of systems using ring resonators. The latter is obtained by having a high temporal resolution, which is possible when using a broadband light source with a parallel readout of a plurality of, and optimally all of the channels at the same time.

According to some embodiments of the present invention, the system 100 furthermore comprises a radiation source 120. The radiation source 120 advantageously is a broad spectrum radiation source. Examples of such sources are white emitting light sources, such as white leds, superluminescent leds, supercontinuum sources, etc. Where in embodiments of the present invention broad spectrum radiation source is used, reference is made to a radiation source spanning at least a range of 2 nm. In some embodiments, the radiation source 120 also may be integrated on the substrate, e.g. homogeneous or heterogeneous.

According to some embodiments of the present invention, the system 100 furthermore comprises a read-out means (not shown in FIG. 3) for reading out a multiple of channels, e.g. all channels of the spectrum analyser in parallel. The latter results in an advantageously fast read out, allowing e.g. to use averaging and thus reducing noise. In one example, the read-out means may be a multiple pixel camera for imaging output couplers in each of the channels of the spectrum analyser in parallel. Such a camera or detector also can be integrated in the substrate.

Further optional features, typically present in a sensing system and known to the person skilled in the art, also may be present in the system, embodiments of the present invention not being limited thereby.

In a second aspect, the present invention also relates to a system for detecting a biological, chemical, biomimic or biochemical target analyte in a medium. Such a system may comprise a photonics integrated system as described above. Additionally other optional components also may be present. In one set of embodiments, the system furthermore comprises a processor for processing the spectral data obtained using the photonics integrated system.

In yet another aspect, the present invention relates to the use of a photonics integrated system according to embodiments of the first aspect or according to a detection system according to the second aspect, for detection of analytes in a specimen. The analytes of interest can actually be any type of analytes, and the sensor may be adapted thereto, e.g. by functionalizing a region of the substrate of the sensor. An advantage of a method of using the photonics integrated system may be that parallel processing of the different channels of the spectral filter may be performed, allowing to reduce the time required for analyzing the result. The latter can advantageously be used for example to reduce noise, by averaging over different measurements.

By way of illustration, embodiments of the present invention not being limited thereto, a particular example of a lab-on-chip integrated photonics sensor is described below.

The exemplary system is based on 450 nm-wide single-mode waveguides defined in a 220 nm high silicon top layer of a semiconductor on insulator wafer with a 2 µm buried oxide. The structures were implemented using CMOS-compatible 193 nm optical lithography and dry etching. A 600 nm-thick cladding of a benzocyclobutene based polymer with low water absorption covers the complete chip except for a window to a second resonator. The window opening can be chosen thus determining the sensitivity of the sensor (the longer the window, the longer the light is in contact with the detection region, however the increasing propagation losses limit the maximal window size). In the present example a length of 4 mm was selected. The window was optimized so that the sensor would have a large sensitivity, while retaining acceptable propagation losses. The arms of the Mach-Zehnder interferometer (MZI) are folded to reduce their footprint. The arrayed waveguide grating AWG has 16 channels with 1.6 nm spacing. The selected dimensions fulfill the requirements for obtaining a bandwidth being larger than the period of the MZI, thus avoiding that it is limiting the sensor's dynamic range. To couple radiation from and to the device, the input and output waveguides were adiabatically tapered to a 10 µm-wide ridge waveguide in which a second-order grating was etched to diffract TE-polarized light out-of-plane. The relative power diffracted to free space by all output gratings, each corresponding with a channel of the AWG, was monitored in parallel using a near-infrared camera with a microscope objective at a distance of several centimeters from the chip. A standard single-mode optical fiber was butt-coupled to the input grating.

The exemplary system as described above allows monitoring refractive index changes fast and accurately, despite the limited spectral resolution of the AWG and the corresponding inaccuracy of the spectrum fitting. As the refractive index changes in label-free biosensing are typically slow compared to the period with which the spectra can be captured with a camera, the noise on the peak position signal can be reduced by smoothening the signal with a moving average over a time scale corresponding to the speed of the refractive index changes of interest. Based on the central limit theorem in statistics, it can be expected that the standard deviation on the signal will be reduced by the square root of the amount of spectra in the chosen window.

The invention claimed is:

1. A photonics integrated system, the photonics integrated system comprising
a substrate,
an integrated interferometer integrated in the substrate and being configured for receiving radiation from an optical radiation source, and
an integrated spectral filter integrated in the substrate and being configured for receiving radiation from the interferometer,
wherein the integrated interferometer has a period and the integrated spectral filter has a bandwidth such that the period of the integrated interferometer is smaller than the bandwidth of the integrated spectral filter,
wherein the integrated spectral filter has a periodic transfer characteristic with a period and the system has a bandwidth such that the period of the periodic transfer characteristic of the integrated spectral filter is larger than the bandwidth of the system, and
wherein the system furthermore comprises a read-out means for reading out a multiple of channels of the spectrum analyser in parallel.

2. A photonics integrated system according to claim 1, wherein the integrated interferometer is a Mach-Zehnder interferometer.

3. A photonics integrated system according to claim 1, wherein the integrated spectral filter is an arrayed waveguide grating.

4. A photonics integrated system according to claim 1, the photonics integrated system comprising an integrated spectral analyser comprising the integrated spectral filter.

5. A photonics integrated system according to claim 1, wherein the read-out means is a multiple pixel camera for imaging output couplers in each of the channels of the spectrum analyser in parallel.

6. A photonics integrated system according to claim 1, wherein the system furthermore comprises an integrated radiation source integrated in the substrate configured for providing radiation to the integrated interferometer.

7. A photonics integrated system according to claim 1, wherein the radiation source is a broad band radiation source.

8. A photonics integrated system according to claim 1, the system being a sensor, wherein the integrated interferometer comprises at least a first radiation waveguide and a second radiation waveguide split off from a common radiation path upstream and recombined in a single path downstream, and whereby the first radiation waveguide is configured as a sensing region for interaction with an analyte to be studied and the second radiation waveguide is configured to be screened off from the analyte to be studied.

9. A photonics integrated system according to claim 8, wherein the sensing region comprises receptors for target analytes of interest.

10. A photonics integrated system according to claim 8, wherein the first and/or the second radiation waveguide are folded or curved waveguides.

11. A photonics integrated system according to claim 1, wherein the bandwidth of the system is configured to detect a biological, chemical, biomimic or biochemical target analyte in a medium.

12. A method for detecting analytes in a specimen, the method comprising:
sending radiation from an optical radiation source into a system with a predetermined bandwidth, comprising an interferometer with a predetermined period, the interferometer being integrated in a substrate;
separating radiation into a reference arm and a sensing arm, the sensing arm including a sensing region wherein radiation can interact with analytes;
recombining the radiation from the reference arm and the sensing arm to obtain an interference pattern including a phase difference that depends on a refractive index of the sensing region; and
receiving radiation from the interferometer to a spectral filter with a predetermined bandwidth, the spectral filter being integrated in the substrate, the spectral filter further comprising a periodic transfer characteristic,
wherein the period of the interferometer is smaller than the bandwidth of the spectral filter, and
wherein the period of the periodic transfer characteristic of the spectral filter is larger than the predetermined bandwidth of the system.

13. The method according to claim 12, wherein the spectral filter and the interferometer form a spectral analyser, and the method further comprises reading out, by read-out means, multiple channels of the spectrum analyser.

* * * * *